United States Patent
Fang et al.

(10) Patent No.: US 10,380,731 B1
(45) Date of Patent: Aug. 13, 2019

(54) METHOD AND SYSTEM FOR FAST INSPECTING DEFECTS

(71) Applicant: Hermes Microvision Inc., Hsinchu (TW)

(72) Inventors: Wei Fang, Milpitas, CA (US); Jack Jau, Los Altos Hills, CA (US)

(73) Assignee: HERMES MICROVISION INC., Hsinchu (TW)

(*) Notice: Subject to any disclaimer, the term of this patent is extended or adjusted under 35 U.S.C. 154(b) by 0 days.

(21) Appl. No.: 14/697,066

(22) Filed: Apr. 27, 2015

Related U.S. Application Data

(62) Division of application No. 14/268,213, filed on May 2, 2014, now Pat. No. 9,541,824, which is a division of application No. 13/154,483, filed on Jun. 7, 2011, now Pat. No. 9,494,856.

(51) Int. Cl.
| | | |
|---|---|---|
| *H01J 37/28* | (2006.01) | |
| *G06T 7/00* | (2017.01) | |
| *H01J 37/22* | (2006.01) | |
| *G01N 23/2251* | (2018.01) | |

(52) U.S. Cl.
CPC ........ *G06T 7/0008* (2013.01); *G01N 23/2251* (2013.01); *H01J 37/222* (2013.01); *G06T 2207/10061* (2013.01); *G06T 2207/30148* (2013.01); *H01J 2237/2448* (2013.01); *H01J 2237/2806* (2013.01)

(58) Field of Classification Search
CPC ....... G06T 7/0004–001; G01N 23/2251; H01J 2237/2817; H01J 37/28; H01J 2237/24592; H01J 37/222; G01T 7/0008; G01T 2207/10061; G01T 2207/30146
See application file for complete search history.

(56) References Cited

U.S. PATENT DOCUMENTS

| | | |
|---|---|---|
| 4,532,650 A | 7/1985 | Wihl et al. |
| 4,755,874 A | 7/1988 | Esrig et al. |
| 4,771,468 A | 9/1988 | Batchelder et al. |
| 4,805,123 A | 2/1989 | Specht et al. |
| 4,845,558 A | 7/1989 | Tsai et al. |
| 5,452,368 A | 9/1995 | Lebeau |
| 5,513,275 A | 4/1996 | Khalalj et al. |
| 5,578,821 A | 11/1996 | Meisberger et al. |
| 5,699,447 A | 12/1997 | Alumot et al. |
| 5,943,437 A | 8/1999 | Sumie et al. |
| 5,978,501 A | 11/1999 | Badger et al. |
| 6,128,404 A | 10/2000 | LeBeau |
| 6,175,646 B1 | 1/2001 | Schemmel et al. |
| 6,246,787 B1 | 6/2001 | Hennessey et al. |

(Continued)

OTHER PUBLICATIONS

Mictronic (Mictronic webpage citing EAGLEview. Microtronic is manufacturer of EAGLEview inspection tool—pp. 1-14). Printed on Aug. 15, 2015.

*Primary Examiner* — Eliza W Osenbaugh-Stewart
(74) *Attorney, Agent, or Firm* — Finnegan, Henderson, Farabow, Garrett & Dunner, LLP

(57) ABSTRACT

A method and system for inspecting defects saves scanned raw data as an original image so as to save time for repeated scanning and achieve faster defect inspection and lower false rate by reviewing suspicious defects and other regions of interest in the original image by using the same or different image-processing algorithm with the same or different parameters.

7 Claims, 6 Drawing Sheets

(56) References Cited

U.S. PATENT DOCUMENTS

| | | | |
|---|---|---|---|
| 6,268,093 B1 | 7/2001 | Kenan et al. | |
| 6,366,688 B1 * | 4/2002 | Jun | G01R 31/2886 |
| | | | 250/311 |
| 6,396,945 B1 | 5/2002 | Ishii | |
| 6,400,839 B1 | 6/2002 | Takayama | |
| 6,504,947 B1 | 1/2003 | Nozaki et al. | |
| 6,614,520 B1 | 9/2003 | Bareket et al. | |
| 6,738,506 B2 | 5/2004 | Miller et al. | |
| 7,508,973 B2 | 3/2009 | Okabe et al. | |
| 7,855,088 B2 | 12/2010 | Akomer et al. | |
| 8,106,355 B1 * | 1/2012 | Lauber | H01J 37/28 |
| | | | 250/306 |
| 8,139,843 B2 | 3/2012 | Kulkarni et al. | |
| 9,494,856 B1 * | 11/2016 | Fang | G03F 1/86 |
| 9,541,824 B1 | 1/2017 | Fang et al. | |
| 2003/0076989 A1 | 4/2003 | Maayah et al. | |
| 2007/0286473 A1 | 12/2007 | Leslie et al. | |
| 2008/0317329 A1 * | 12/2008 | Shibuya | G06T 7/0004 |
| | | | 382/149 |
| 2009/0080759 A1 | 3/2009 | Bhaskar et al. | |
| 2012/0145894 A1 | 6/2012 | Wu et al. | |
| 2013/0082177 A1 * | 4/2013 | Hiroi | G01N 23/2251 |
| | | | 250/310 |

\* cited by examiner

METHOD AND SYSTEM FOR FAST INSPECTING DEFECTS

RELATED APPLICATION

This Application is a Divisional Application of U.S. application Ser. No. 14/268,213, filed on May 2, 2014, which is a Divisional Application of U.S. application Ser. No. 13/154,483, filed on Jun. 7, 2011, the entire contents of which are incorporated herein by reference.

BACKGROUND OF THE INVENTION

Field of the Invention

The present invention relates to a method and system for inspecting defects, and more particularly to a method and system for fast inspecting defects which decreases false rate of defect inspection.

Description of the Prior Art

Defect inspection in the semiconductor device has always been one of important issues in semiconductor manufacturing process. Referring to FIG. 1, a conventional method for inspecting defects is achieved by obtaining a scanned image, e.g. an SEM (scanning electron microscope) image of a specimen such as a semiconductor device (S11) and identifying defects on the surface of the specimen within the scanned image (S12). Since the scanned data is of extremely enormous data volume and often larger than 20 TB (terabyte), the scanned data would be discarded after defect inspection (S13). In the case of requiring further verification for defects (S14), then return to step S11 and the specimen is rescanned for defect analysis. Referring to FIG. 2, to be brief, the conventional method for inspecting defects alternates between specimen scanning and data analysis.

Some identified suspicious defects might be not real defects and a false rate is used for representing the accuracy of defect inspection. The false rate has kept increasing due to sustained trend of minimized semiconductor manufacturing process and tremendously increased scanned data. The false rate may be improved by enhancing scanning resolution of E-beam inspection tools and rescanning all of regions of interest in the same specimen; however, the scanning time and scanned data would be greatly increased due to the enhanced scanning resolution of E-beam inspection tools. In addition to increased inspection time, rescanning might also encounter certain issues, such as missing real defects and misjudging non-defects, caused by varied scanning conditions. For example, the charge condition of the surface of the specimen might be changed at first E-beam scanning and results in variation in the scanned image obtained at the second E-beam scanning and biased result of defect inspection.

To sum up, it is now a current goal to lower false rate of defect inspection.

SUMMARY OF THE INVENTION

The present invention is directed to a method and system for inspecting defects which saves scanned raw data as an original image so as to save time for repeated scanning and achieve faster defect inspection and lower false rate by reviewing suspicious defects and other regions of interest in the original image by using the same or different image-processing algorithm with the same or different parameters.

In first embodiment of the present invention, a method for fast identifying defects includes scanning a specimen to generate an original image and locations of regions of interest and reviewing the locations on the original image to identify defects.

In second embodiment of the present invention, a method for decreasing false rate in defect inspection includes providing locations of regions of interest of a specimen by scanning a surface of the specimen; saving scanned raw data as an original image; and reviewing the locations on the original image to identify defects on the surface.

In third embodiment of the present invention, a method for fast inspecting defects includes scanning a surface of a wafer; identifying suspicious defects or critical patterns by using a first image-processing algorithm with a first set of parameters; saving scanned raw data from the scanning step as an original image; identifying hot spots according to the suspicious defects or the critical patterns; marking locations of the hot spots; and reviewing the locations on the original image to identify defects on the surface.

In fourth embodiment of the present invention, a computer readable medium encoded with a computer program implementing a method for fast inspecting defects. The method comprises steps of scanning a surface of a wafer; identifying suspicious defects or critical patterns by using a first image-processing algorithm with a first set of parameters; saving scanned raw data from the scanning step as an original image; identifying hot spots according to the suspicious defects or the critical patterns; marking locations of the hot spots; and reviewing the locations on the original image to identify defects on the surface.

In fifth embodiment of the present invention, a system for fast inspecting defects includes a charged particle beam probe, a charged particle beam deflection module, an image forming apparatus, a storage module and a defect inspection module. The charged particle beam probe generator is configured for generating a charged particle beam probe. The charged particle beam deflection module is configured for scanning the charged particle beam probe across a surface of a wafer. The image forming apparatus is configured for detecting secondary charged particles emitted from the surface of the region of interest being bombarded by the charged particle beam probe and forming at least one scanned raw image accordingly. The storage module is configured for saving the scanned raw image as an original image. The defect inspection module encoded with a computer program is configured implementing a method for fast inspecting defects. The method includes steps of identifying suspicious defects or critical patterns on the scanned raw image by using a first image-processing algorithm with a first set of parameters; identifying hot spots according to the suspicious defects or the critical patterns; marking locations of the hot spots; and reviewing the locations on the original image to identify defects on the surface.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

The specimen hereafter described will be referred to wafer or reticle, wherein the reticle is used in lithography. Wafer may include silicon wafer, silicon-germanium wafer, SOI wafer, or III-V or II-VI compound semiconductor wafer. This invention can be also applied to reticle inspection, especially EUV mask inspection.

Figure 1:
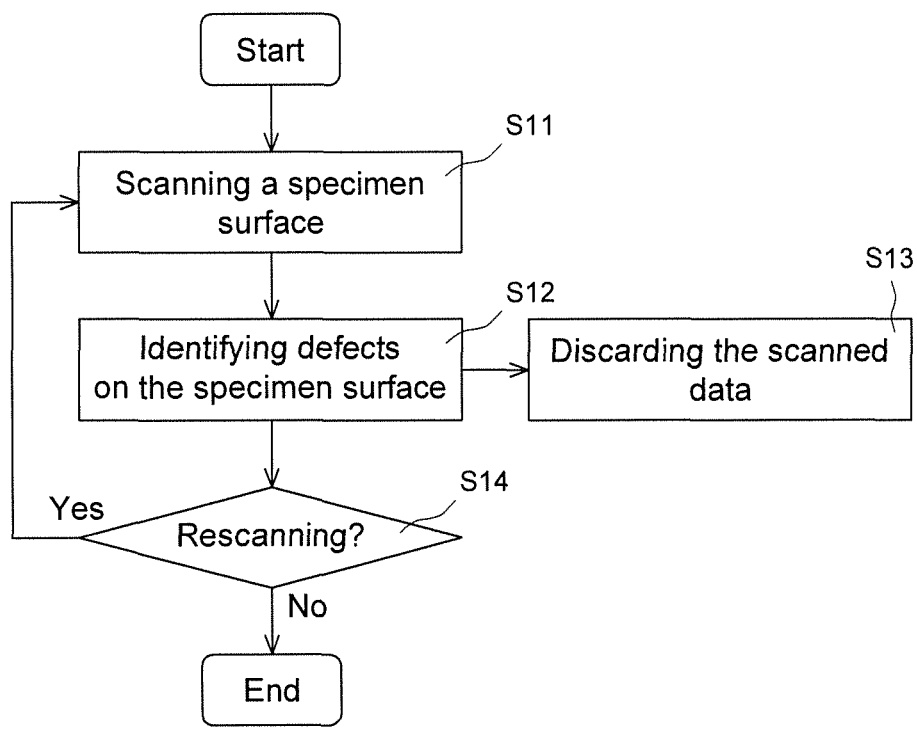
FIG. 1 is a flow chart schematically illustrating a method for inspecting defects according to a prior art.
Figure 2:
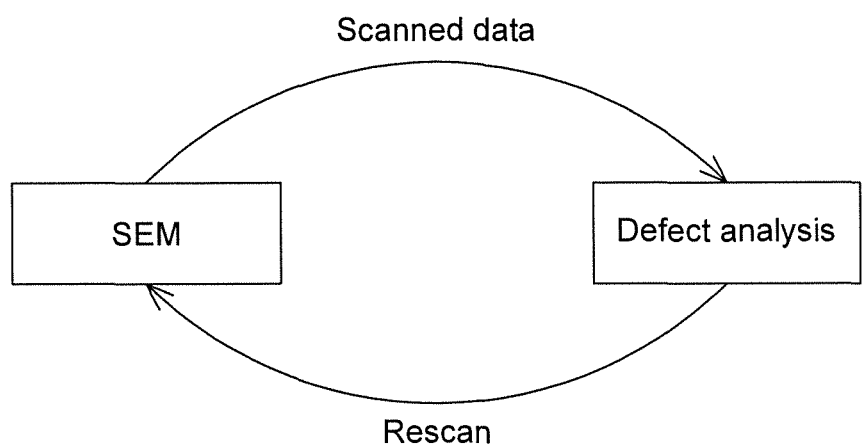
FIG. 2 is a diagram schematically illustrating a method for inspecting defects according to a prior art.
Figure 3:
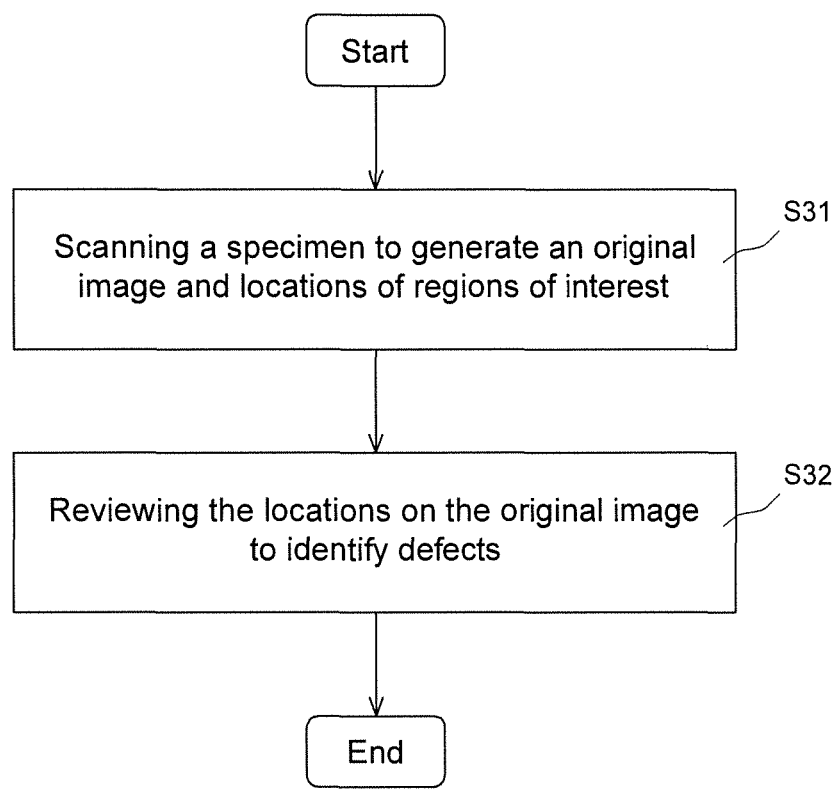
FIG. 3 is a flow chart schematically illustrating a method for fast identifying defects according to an embodiment of the present invention.
Figure 4:
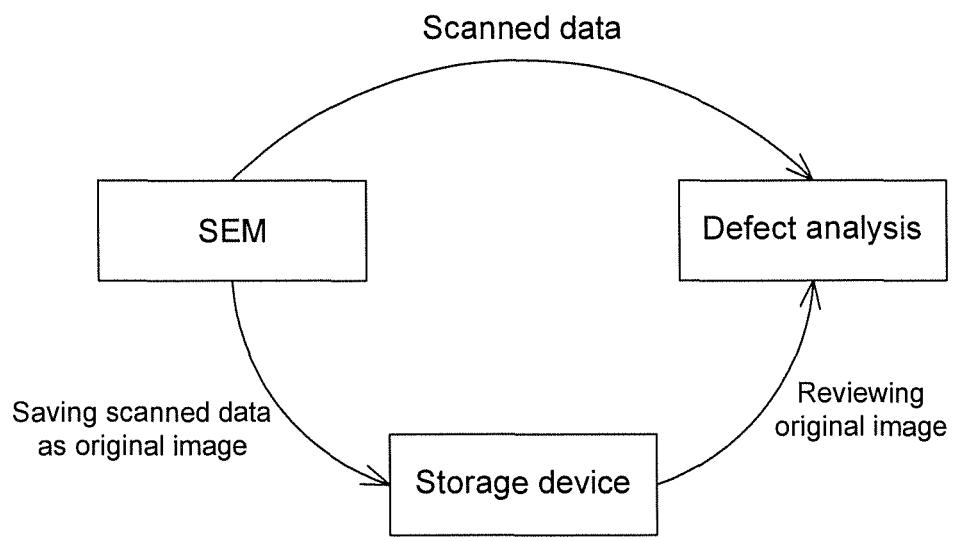
FIG. 4 is a diagram schematically illustrating a method for fast identifying defects according to an embodiment of the present invention.

Referring to FIG. 3, a method for fast identifying defects according to an embodiment of the present invention includes scanning a specimen to generate an original image and locations of regions of interest (S31) and reviewing the locations on the original image to identify defects (S32). In one embodiment, the scanning step is processed by using an E-beam inspection tool or an optical inspection tool. Also referring to FIG. 4, the scanned raw data is saved as an original image and stored in a storage device. In addition, the scanned raw data is also used for identifying defects so as to identify locations of regions of interest.

Figure 5:
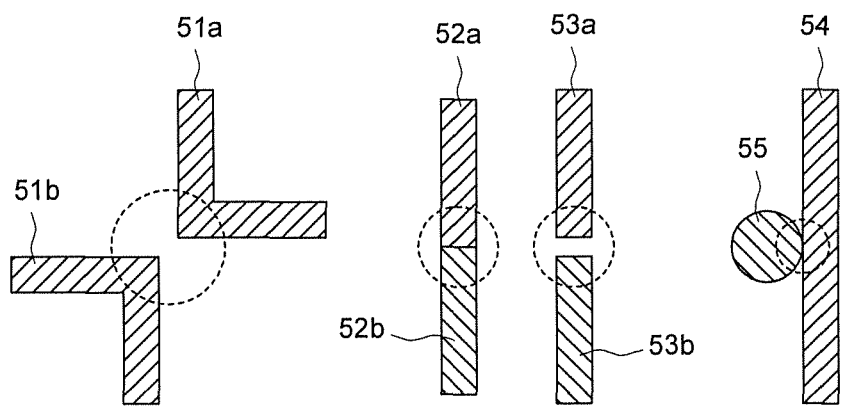
FIG. 5 is a diagram schematically illustrating a plurality of examples of critical pattern.

In one embodiment, the scanned image is compared to the original design or predetermined patterns, such as GDS (Graphic Data System) or OASIS (open Artwork System Interchange Standard), or the scanned images are compared to each other so as to obtain regions of interest. The regions of interest include suspicious defects, real defects or critical patterns, wherein the suspicious defects include real defects and non-defects. Referring to FIG. 5, the critical patterns, for example, may be referred as pitch of corners of traces 51a, 51b, connection between traces 52a, 52b, pitch of traces 53a, 53b and connection between trace 54 and electrode 55. In one embodiment, the regions of interest are obtained by following steps including identifying suspicious defects or critical patterns by using a first image-processing algorithm with a first set of parameters; identifying hot spots according to the suspicious defects or the critical patterns; and marking locations of the hot spots. It is noted that the hot spots may include suspicious defects, real defects or critical patterns; alternatively, the hot spots may be an area that may be resulted in the above-mentioned defects or an area having defect caused by the above-mentioned defects.

It is noted that the original image stored in the storage device may be reviewed directly for further defect analysis without scanning specimens again. In one embodiment, the same or different types of image-processing algorithm and parameters may be utilized for the reviewing the original image. For example, the reviewing step may utilize the first image-processing algorithm with a second set of parameters different from the first set of parameters; or the reviewing step may utilize a second image-processing algorithm different from the first image-processing algorithm with the first set of parameters or the second set of parameters.

According to the above-mentioned, saving the scanned raw data as the original image may save time for repeated scanning and prevent the difference of scanning results caused by different scanning conditions in the second scanning. In addition, the original image may be reproduced or divided for simultaneously performing a plurality of defect analysis so as to achieve shortened defect inspection time and decreased false rate in defect inspection.

Figure 6:
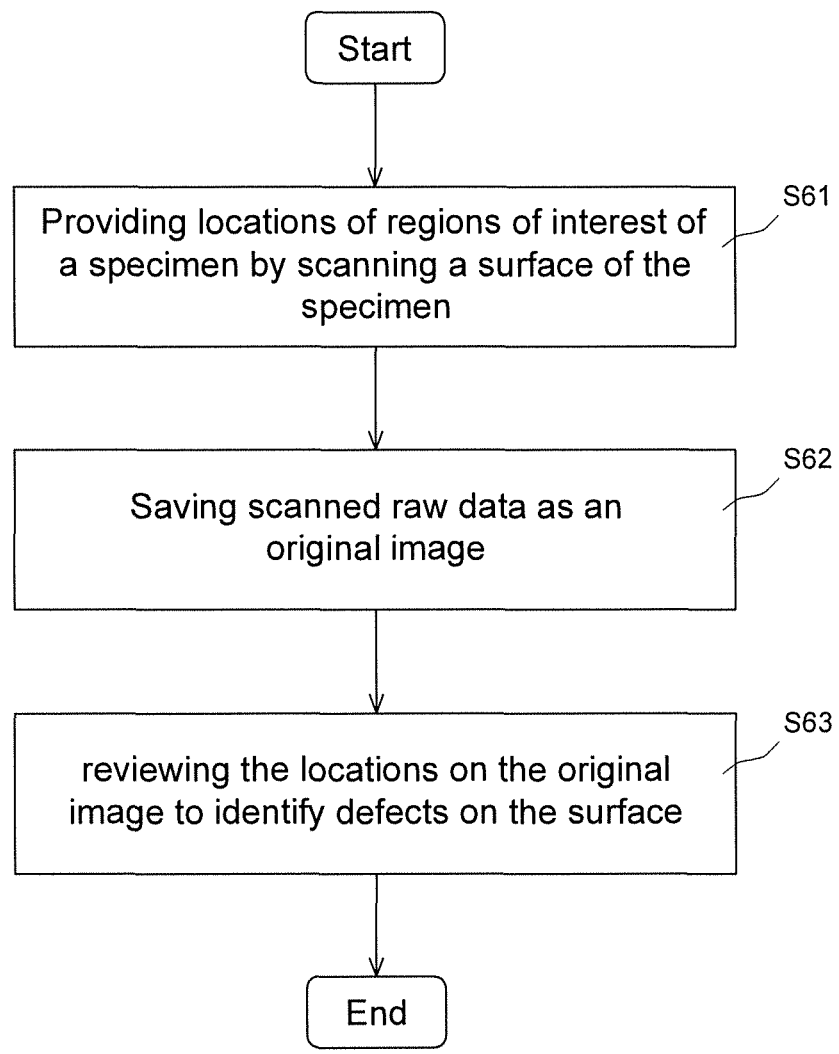
FIG. 6 is a flow chart schematically illustrating a method for decreasing false rate in defect inspection according to an embodiment of the present invention.

Referring to FIG. 6, a method for decreasing false rate in defect inspection according to one embodiment of the present invention includes providing locations of regions of interest of a specimen by scanning a surface of the specimen (S61); saving scanned raw data as an original image (S62); and reviewing the locations on the original image to identify defects on the surface (S63). According to the above-mentioned, the scanning step for scanning a surface of the specimen may be processed by using an E-beam inspection tool or an optical inspection tool, and the types of algorithm and parameters used for identifying locations of regions of interest in the specimen and locations of regions of interest in the reviewed original data may be the same or different.

In one embodiment, the specimen may be a wafer including a plurality of dies thereon, and the regions of interest are identified in one die of the plurality of dies. In the reviewing step, not only the locations of regions of interest in the previously reviewed dies as well as other locations in addition to those are reviewed but all other dies on the original image are reviewed. For example, in the case of finding a real defect in one die, the correspondent locations in other dies in the original image are also reviewed for identifying the similar defects in other dies.

Figure 7:
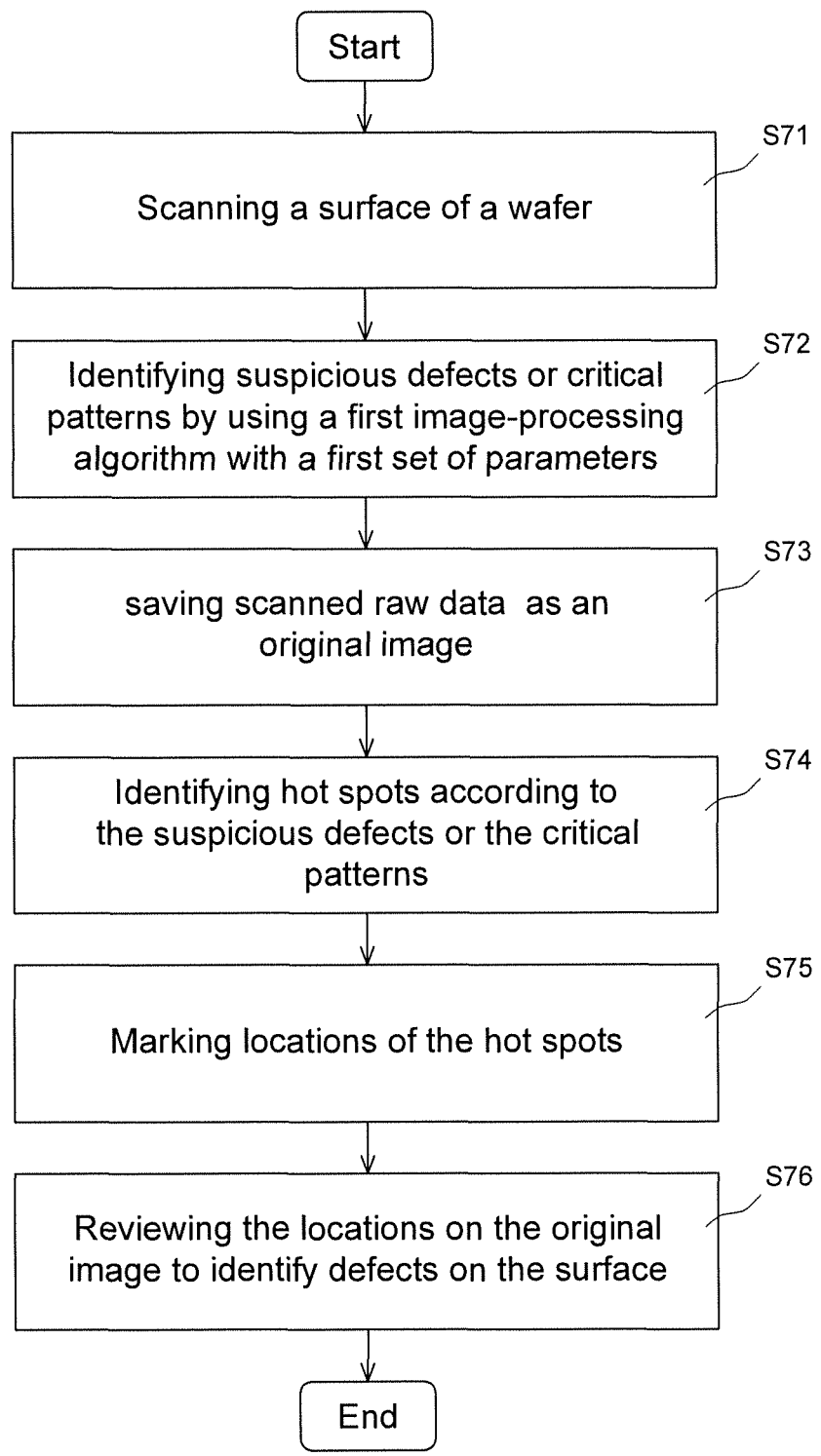
FIG. 7 is a flow chart schematically illustrating a method for fast inspecting defects according to an embodiment of the present invention.

Refer to FIG. 7, which illustrates a method for fast inspecting defects according to one embodiment of the present invention. Firstly, a surface of a wafer is scanned by using an E-beam inspection tool or an optical inspection tool (S71). Suspicious defects or critical patterns are then identified by using a first image-processing algorithm with a first set of parameters (S72). In addition, the scanned raw data from the scanning step S71 is saved as an original image (S73). Hot spots according to the suspicious defects or the critical patterns are then identified (S74), and locations of the hot spots are marked (S75). At last, the locations on the original image are reviewed to identify defects on the surface (S76).

Those skilled in the art of the present invention may understand how to analyze the existence of specific defects in wafers by adopting specific image-processing algorithm and parameters. Therefore, the original image may be reviewed with combination of the same or different image-processing algorithm and parameters for analyzing defects therein. In addition, the wafer also includes a plurality of dies on the wafer, and suspicious defects or critical patterns may be identified from one of the plurality of dies. The locations of hot spots in the plurality of dies and all other dies in the original images may be reviewed when reviewing the original images.

A computer readable medium according to one embodiment of the present invention is encoded with a computer program. The computer program is configured for implementing the method for fast inspecting defects as illustrated in FIG. 7, wherein the detailed steps has been previously mentioned and hence abbreviated herein.

Figure 8:
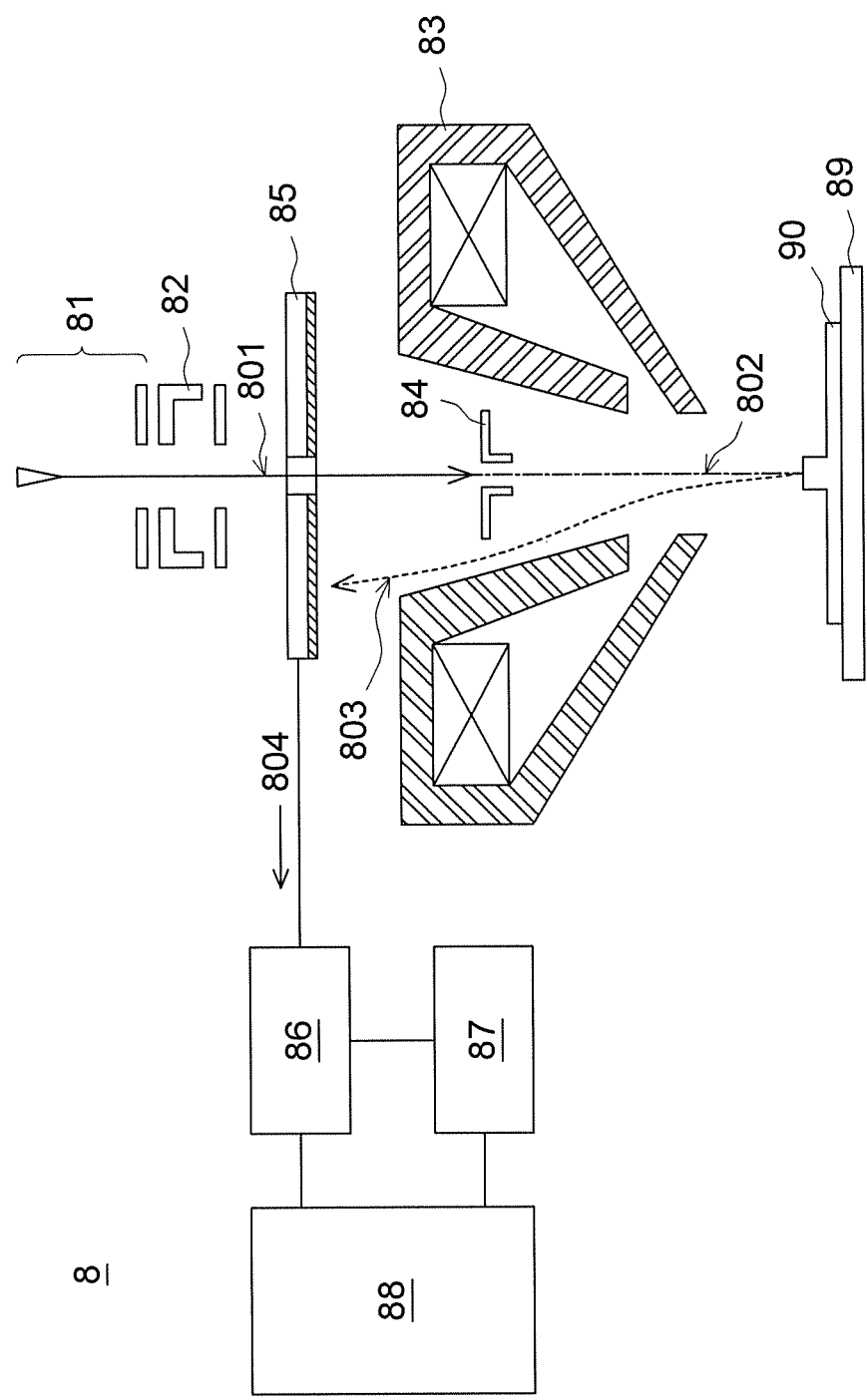
FIG. 8 is a diagram schematically illustrating a system for fast inspecting defects according to an embodiment of the present invention.

Referring to FIG. 8, which illustrates a system 8 for fast inspecting defects according to an embodiment of the present invention. The system 8 is used for inspecting a sample 90 (such as a wafer) on a sample stage 89 and comprises a charged particle beam generator 81, a condenser lens module 82, a probe forming objective lens module 83, a charged particle beam deflection module 84, a secondary charged particle detector module 85, an image forming module 86, a storage module 87 and a defect inspecting module 88.

The charged particle beam generator 81 is used for generating a primary charged particle beam 801. The condenser lens module 82 is used for condensing the generated primary charged particle beam 801. The probe forming objective lens module 83 is used for focusing the condensed primary charged particle beam into a charged particle beam probe 802. The charged particle beam deflection module 84 is used for scanning the formed charged particle beam probe 802 across surfaces of the sample 90 secured on the sample stage 89. In one embodiment, the charged particle beam generator 81, the condenser lens module 82 and the probe forming objective lens module 83, or their equivalent designs, alternatives or any combination thereof, together form a charged particle beam probe generator which generates the scanning charged particle beam probe 802.

The secondary charged particle detector module 85 is used for detecting secondary charged particles 803 emitted from the sample surface (may also be along with other reflected or scattered charged particles from the sample surface) upon being bombarded by the charged particle beam probe 802 to generate a secondary charged particle detection signal 804. The image forming module 86 is coupled with the secondary charged particle detector module 85 for receiving the secondary charged particle detection signal 804 from the secondary charged particle detector module 85 and forming at least one scanned raw image accordingly.

The image forming module 86 may be a mainframe host, terminals, personal computers, any kind of mobile computing devices or combination thereof. In addition, the image forming module 86 may connect with the secondary charged particle detector module 85 through a medium selected from the following: cable wire, optical fiber cable, portable storage media, IR, Bluetooth, intranet, internet, wireless network, wireless radio, and any combination thereof. In one embodiment, secondary charged particle detector module 85 and image forming module 86, or their equivalent designs, alternatives or any combination thereof, together form an image forming apparatus which forms a scanned raw image from detected secondary charged particles emitted from sample 90 being bombarded by the charged particle beam probe 802. The storage module 87 is coupled with the image forming apparatus and used for saving the scanned raw image as an original image.

The above components of the system are well known to those skilled in the art and are not presented here to limit the scope of the present invention. Alternatives and insubstantial modifications of these components should be construed equivalent to the disclosure of the present invention.

The defect inspecting module 88 is coupled to the image forming module 86 of the image forming apparatus and the storage module 87 to inspect defects on the sample 90 within the scanned raw image received from the image forming module 86 and/or the original image received from the storage module 87. In one embodiment, the defect inspecting module 88 connects to and accesses the image forming apparatus and the storage module 87 through a medium selected from the following: cable wire, optical fiber cable, portable storage media, IR, manual input of humans, Bluetooth, intranet, internet, wireless network, wireless radio, and any combination thereof. Further, the defect inspecting module 88 may be implemented as one selected from the following: a mainframe host, a terminal computer, a personal computer, any kind of mobile computing devices, and any combination thereof. In one embodiment, a computer program for fast inspecting defects is encoded on a computer readable medium disposed within the defect inspecting module 88 so that the defect inspecting module 88 is able to perform the steps of fast inspecting defects illustrated in conjunction with FIG. 7, wherein the details of the steps of fast inspecting defects is described earlier.

To sum up, the method and system for fast inspecting defects of the present invention saves scanned raw data as an original image so as to save time for repeated scanning and achieve faster defect inspection and lower false rate by reviewing suspicious defects and other regions of interest in the original image by using the same or different image-processing algorithm with the same or different parameters.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A system for fast inspecting defects, comprising:
a charged particle beam probe generator for generating a charged particle beam probe;
a charged particle beam deflection module for deflecting the charged particle beam probe to scan across an area on a surface of a wafer, wherein the area includes one or more dies;
an image forming apparatus for detecting secondary charged particles emitted from the surface of the region of interest being bombarded by the charged particle beam probe and forming at least one scanned raw image of the area accordingly;
a storage module for saving the scanned raw image as an original image;
a defect inspection module encoded with a computer program configured to cause the defect inspection module to
identify defects on the scanned raw image by using a first image-processing algorithm with a first set of parameters; and
provide a list of locations on the scanned raw image that correspond to the defects for storing; and
a defect review module encoded with a computer program configured to cause the defect review module to review the locations on the original image to analyze the defects on the surface by
a first defect analysis that uses the first image-processing algorithm with a second set of parameters different from the first set of parameters; and a second defect analysis that uses a second image-processing algorithm different from the first image-processing algorithm,
wherein the review of the locations on the original image comprises reproducing or dividing the original image and simultaneously performing the first defect analysis and the second defect analysis.

2. The system according to claim 1, wherein the wafer includes a plurality of dies thereon.

3. The system according to claim 2, wherein the defects are identified in one die of the plurality of dies.

4. The system according to claim 3, wherein the review of the locations on the original image comprises a review of the locations of each of the plurality of dies on the original image.

5. The system according to claim 3, wherein the review of the locations on the original image comprises a review of the locations of each of all other dies on the original image.

6. The system according to claim 1, wherein the wafer includes a plurality of dies and the defects on the at least one scanned raw image include locations at two or more of the plurality of dies.

7. The system according to claim 1, wherein the original image is greater than or equal to 20 tera-bytes.

* * * * *